United States Patent
Lee

(10) Patent No.: US 11,715,817 B2
(45) Date of Patent: Aug. 1, 2023

(54) LIGHT-EMITTING ELEMENT PACKAGE AND LIGHT-EMITTING ELEMENT MODULE INCLUDING SAME

(71) Applicant: SUZHOU LEKIN SEMICONDUCTOR CO., LTD., Taicang (CN)

(72) Inventor: Koh Eun Lee, Seoul (KR)

(73) Assignee: SUZHOU LEKIN SEMICONDUCTOR CO., LTD., Suzhou (CN)

( * ) Notice: Subject to any disclaimer, the term of this patent is extended or adjusted under 35 U.S.C. 154(b) by 0 days.

(21) Appl. No.: 17/052,182

(22) PCT Filed: Mar. 4, 2019

(86) PCT No.: PCT/KR2019/002474
§ 371 (c)(1),
(2) Date: Oct. 31, 2020

(87) PCT Pub. No.: WO2019/212136
PCT Pub. Date: Nov. 7, 2019

(65) Prior Publication Data
US 2021/0305465 A1     Sep. 30, 2021

(30) Foreign Application Priority Data
May 3, 2018   (KR) .................. 10-2018-0051257

(51) Int. Cl.
*H01L 33/48*   (2010.01)
*H01L 33/62*   (2010.01)
(Continued)

(52) U.S. Cl.
CPC .............. *H01L 33/486* (2013.01); *A61L 2/10* (2013.01); *A61L 2/26* (2013.01); *A61L 9/20* (2013.01);
(Continued)

(58) Field of Classification Search
CPC ....... H01L 33/64; H01L 33/62; H01L 33/644; H01L 33/486; H01L 33/647;
(Continued)

(56) References Cited

U.S. PATENT DOCUMENTS 9,240,524 B2 * 1/2016  Park ................. H01L 33/48
9,378,986 B2 * 6/2016  Ahn .................. H01L 21/563
(Continued)

FOREIGN PATENT DOCUMENTS

EP       3451396 A1 *  3/2019 ........... H01L 33/486
JP       2011-035264    2/2011
(Continued)

OTHER PUBLICATIONS

WO-2016167625-A2 English translation, Oct. 2016, Cha S J, pp. 1-10.*
(Continued)

*Primary Examiner* — Latanya N Crawford Eason
(74) *Attorney, Agent, or Firm* — Birch, Stewart, Kolasch & Birch, LLP

(57) ABSTRACT

Disclosed in an embodiment is a light-emitting element package comprising: a body including a cavity; a light-emitting element arranged on the bottom surface of the cavity and including a first conductive type semiconductor layer, a second conductive type semiconductor layer and an active layer, which is arranged between the first conductive type semiconductor layer and the second conductive type semiconductor layer; and a light-transmitting member arranged on the upper part of the cavity, wherein the body includes: a lower body including the bottom surface of the
(Continued)

cavity; an upper body including the lateral surface of the cavity; and a first insulating layer arranged between the lower body and the upper body, the lower body includes a first conductive body and a second conductive body insulated and arranged together with the first conductive body, the first conductive type semiconductor layer is electrically connected with the first conductive body, the second conductive type semiconductor layer is electrically connected with the second conductive body, and the height from the lower surface of the lower body to the bottom surface of the cavity is less than the height from the lower surface of the lower body to the lower surface of the first insulating layer.

18 Claims, 12 Drawing Sheets

(51) Int. Cl.
| | | |
|---|---|---|
| *H01L 33/64* | (2010.01) | |
| *A61L 2/10* | (2006.01) | |
| *A61L 2/26* | (2006.01) | |
| *A61L 9/20* | (2006.01) | |

(52) U.S. Cl.
CPC ............ *H01L 33/62* (2013.01); *H01L 33/644* (2013.01); *A61L 2202/11* (2013.01); *A61L 2202/24* (2013.01); *A61L 2209/12* (2013.01)

(58) Field of Classification Search
CPC ... H01L 23/043; H01L 23/142; H01L 23/429; H01L 33/60; H01L 33/483
See application file for complete search history.

(56) References Cited

U.S. PATENT DOCUMENTS

| | | | | |
|---|---|---|---|---|
| 9,559,276 | B2* | 1/2017 | Ahn | H01L 33/486 |
| 10,714,660 | B2* | 7/2020 | Kim | H01L 33/483 |
| 2015/0001573 | A1* | 1/2015 | Park | H01L 33/486 |
| | | | | 257/99 |
| 2015/0048408 | A1* | 2/2015 | Nam | H01L 33/56 |
| | | | | 257/99 |
| 2015/0243864 | A1* | 8/2015 | Ahn | H01L 24/97 |
| | | | | 257/88 |
| 2016/0111606 | A1* | 4/2016 | Park | H01L 33/62 |
| | | | | 257/98 |
| 2016/0380159 | A1* | 12/2016 | Nam | H01L 33/486 |
| | | | | 257/99 |
| 2017/0256675 | A1* | 9/2017 | Choi | H01L 33/502 |
| 2018/0266649 | A1* | 9/2018 | Kang | H01L 33/502 |
| 2019/0097090 | A1* | 3/2019 | Ahn | H01L 33/486 |
| 2019/0259734 | A1* | 8/2019 | Li | H01L 33/647 |
| 2019/0319178 | A1* | 10/2019 | Ahn | H01L 25/13 |

FOREIGN PATENT DOCUMENTS

| | | | | |
|---|---|---|---|---|
| KR | 10-0287862 | | 6/2001 | |
| KR | 10-1504282 | | 3/2015 | |
| KR | 10-2017-0023478 | | 3/2017 | |
| KR | 10-1715789 | | 3/2017 | |
| WO | WO-2016167625 A2 * | 10/2016 | ............. H01L 33/48 |

OTHER PUBLICATIONS

International Search Report (with English Translation) and Written Opinion dated Jun. 5, 2019 issued in Application No. PCT/KR2019/002474.

* cited by examiner

LIGHT-EMITTING ELEMENT PACKAGE AND LIGHT-EMITTING ELEMENT MODULE INCLUDING SAME

CROSS-REFERENCE TO RELATED PATENT APPLICATIONS

This application is a U.S. National Stage Application under 35 U.S.C. § 371 of PCT Application No. PCT/KR2019/002474, filed Mar. 4, 2019, which claims priority to Korean Patent Application No. 10-2018-0051257, filed May 3, 2018, whose entire disclosures are hereby incorporated by reference.

TECHNICAL FIELD

Embodiments relate to a light-emitting element package and a light-emitting element module including the same.

BACKGROUND ART

Light-emitting elements containing compounds, such as GaN, AlGaN, and the like, have many advantages such as wide and easily adjustable bandgap energy and the like and can be variously used as light-emitting devices, light-receiving devices, various diodes, and the like.

In particular, a light-emitting element such as a light-emitting diode or a laser diode using a Group III-V or II-VI compound semiconductor material may realize various colors, such as red light, green light, and a blue light, ultraviolet rays, and the like, resulting from development of a thin film growth technique and an element material, and white light with high efficiency using a phosphor or by combining colors, and has advantages of low power consumption, a semi-permanent lifetime, a fast response time, safety, and environment friendliness when compared to conventional light sources such as fluorescent lamps and incandescent lamps.

In addition, when a light-receiving device such as a photodetector or a solar cell is manufactured using a Group III-V or II-VI compound semiconductor material, due to development of an element material, the light-receiving device absorbs light in various wavelength bands to generate a photoelectric current so that light in various wavelength bands from gamma rays to a radio wavelength band may be used. Further, with advantages of a fast response speed, safety, environmental friendliness, and easy control of an element material, the light-emitting element can also be easily used for power control, a microwave circuit, or a communication module.

Accordingly, applications of the light-emitting element have expanded to being applied as transmission modules of optical communication devices, light-emitting diode backlights replacing cold cathode fluorescent lamps (CCFLs) forming backlights of liquid crystal display (LCD) devices, white light-emitting diode lighting devices capable of replacing fluorescent lamps or incandescent lamps, headlights of vehicles, traffic lights, sensors for detecting a gas or fire, and the like. In addition, the application of the light-emitting element may be expanded to high frequency application circuits, other power control devices, and communication modules.

In particular, light-emitting devices emitting light in an ultraviolet wavelength band can be used for curing, medical uses, and sterilization by performing a curing and sterilization action.

Meanwhile, when light-emitting elements are designed, thermal dissipation can be an important consideration factor. In addition, when a body of the light-emitting element is made of a metal in order to improve thermal dissipation of the light-emitting element, a design for preventing a short circuit also needs to be made.

SUMMARY

Embodiments are directed to providing a light-emitting element package in which an upper portion of a package body is disposed to be insulated from a lower portion thereof.

Embodiments are also directed to providing a light-emitting element package excellent in thermal dissipation.

Problems to be solved in the embodiments are not limited to the above-described problems, and objects and effects which can be determined from the solutions and the embodiments of the problems described below are also included.

One aspect of the present invention provides a light-emitting element package including a body including a cavity; a light-emitting element disposed on a bottom surface of the cavity and including a first conductive type semiconductor layer, a second conductive type semiconductor layer, and an active layer disposed between the first conductive type semiconductor layer and the second conductive type semiconductor layer; and a light-transmitting member disposed in an upper portion of the cavity, wherein the body includes a lower body including the bottom surface of the cavity, an upper body including a lateral surface of the cavity, and a first insulating layer disposed between the lower body and the upper body, the lower body includes a first conductive body and a second conductive body disposed and insulated from the first conductive body, the first conductive type semiconductor layer is electrically connected to the first conductive body, the second conductive type semiconductor layer is electrically connected to the second conductive body, a height from a lower surface of the lower body to the bottom surface of the cavity is smaller than a height from the lower surface of the lower body to a lower surface of the first insulating layer.

A ratio of the height from a lower surface of the lower body to the bottom surface of the cavity to the height from the lower surface of the lower body to a lower surface of the first insulating layer may range from 1.09:1 to 1.72:1.

Each of the first conductive body and the second conductive body may include a side wall protruding toward the upper body, and the first insulating layer may be disposed on the side wall.

An inner surface of the side wall may be coplanarly connected to an inner surface of the first insulating layer, and an inner surface of the first insulating layer may be coplanarly connected to an inner surface of the upper body.

The lower body may further include a second insulating layer disposed between the first conductive body and the second conductive body.

Each of the first conductive body and the second conductive body may contain aluminum (Al), and the second insulating layer may contain polyimide (PI).

The upper body may include a stepped portion in which the light-transmitting member is disposed.

The first conductive body may include a first groove disposed in a corner at which a lower surface of the first conductive body is connected to a surface thereof facing the second conductive body, and the second conductive body may include a second groove disposed in a corner at which a lower surface of the second conductive body is connected to a surface thereof facing the first conductive body.

The lower body may further include a first insulating portion disposed in the first groove and the second groove.

The first conductive body may include a third groove disposed in a corner at which the lower surface of the first conductive body is connected to an outer surface thereof, and the second conductive body may include a fourth groove disposed in a corner at which the lower surface of the second conductive body is connected to an outer surface thereof.

The lower body may further include a second insulating portion disposed in the third groove and the fourth groove.

The light-emitting element package may further include a sub-mount disposed between the bottom surface of the cavity and the light-emitting element.

The sub-mount may include a first pad and a second pad, a first electrode of the light-emitting element may be electrically connected to the first pad, and a second electrode of the light-emitting element may be electrically connected to the second pad.

The first pad may be electrically connected to the first conductive body through a wire, and the second pad may be electrically connected to the second conductive body through a wire.

Each of a pair of outer surfaces opposite to each other of the body may include a fifth groove, and the fifth groove may be connected to both ends of the second insulating portion in contact with the lower surface of the first conductive body and connected to both ends of the second insulating portion in contact with the lower surface of the second conductive body.

The second insulating portion may include a second-first insulating portion disposed in the third groove and a second-second insulating portion disposed in the fourth groove, and the fifth groove may be disposed between an end portion of the second-first insulating portion and an end portion of the second-second insulating portion.

The upper body may be conductive.

The light-emitting element may emit ultraviolet light.

Another aspect of the present invention provides a light-emitting element package including a body including a cavity; a light-emitting element disposed on a bottom surface of the cavity and including a first conductive type semiconductor layer, a second conductive type semiconductor layer, and an active layer disposed between the first conductive type semiconductor layer and the second conductive type semiconductor layer; and a light-transmitting member disposed in an upper portion of the cavity, wherein the body includes a conductive lower body including a bottom surface of the cavity, a conductive upper body including a lateral surface of the cavity, and a first insulating layer disposed between the conductive lower body and the conductive upper body, the conductive lower body includes a first conductive body and a second conductive body disposed and insulated from the first conductive body, the first conductive type semiconductor layer is electrically connected to the first conductive body, and the second conductive type semiconductor layer is electrically connected to the second conductive body.

Still another aspect of the present invention provides a light-emitting element module including a substrate, a light-emitting element package mounted on the substrate, and a sealing member in contact with an upper surface of the substrate and a lateral surface of the light-emitting element package, wherein the light-emitting element package includes a body including a cavity; a light-emitting element disposed on a bottom surface of the cavity and including a first conductive type semiconductor layer, a second conductive type semiconductor layer, and an active layer disposed between the first conductive type semiconductor layer and the second conductive type semiconductor layer; and a light-transmitting member disposed in an upper portion of the cavity, the body includes a lower body including the bottom surface of the cavity, an upper body including a lateral surface of the cavity, and a first insulating layer disposed between the lower body and the upper body, the lower body includes a first conductive body and a second conductive body disposed and insulated from the first conductive body, the first conductive type semiconductor layer is electrically connected to the first conductive body, and the second conductive type semiconductor layer is electrically connected to the second conductive body, a height from a lower surface of the lower body to the bottom surface of the cavity is smaller than a height from the lower surface of the lower body to a lower surface of the first insulating layer, and a height from the upper surface of the substrate to an upper end of a surface of the sealing member in contact with the body is greater than a height from the upper surface of the substrate to a lower surface of the first insulating layer and is smaller than a height from the upper surface of the substrate to an upper surface of the upper body.

ADVANTAGEOUS EFFECTS

In accordance with a light-emitting element package according to the embodiments, an upper portion of a package body is insulated from a lower portion thereof so that, even when water or chemicals fall on the upper portion, a short circuit can be prevented.

In addition, heat dissipation efficiency of the light-emitting element package can be improved.

Various beneficial advantages and effects of the present invention are not limited by the detailed description and should be easily understood through a description of a detailed embodiment of the present invention.

DETAILED DESCRIPTION

Hereinafter, exemplary embodiments of the present invention will be described in detail with reference to the accompanying drawings.

However, the technical idea of the present invention is not limited to some embodiments to be described but may be implemented in various different forms, and, within the scope of the technical idea of the present invention, one or more among components between embodiments may be used by being selectively combined and substituted.

In addition, unless specifically defined and described, terms used in the embodiments of the present invention (including technical and scientific terms) may be construed as meanings which are generally understood by those skilled in the art to which the present invention pertains, and generally used terms such as terms defined in the dictionary may be interpreted in consideration of the contextual meaning of the related art.

In addition, the terms used in the embodiments of the present invention are intended to describe the embodiments and are not intended to limit the present invention.

In this disclosure, the singular forms may include the plural forms unless the context clearly dictates otherwise, and, when described as "at least one (or one or more) among A, B, and (or) C," it may include one or more among all combinations in which A, B, and C can be combined.

In addition, in describing components of the embodiments of the present invention, the terms first, second, A, B, (a), (b), and the like can be used.

These terms are intended to distinguish one component from other components, but the nature and the order or sequence of the components is not limited by those terms.

In addition, when a component is described as being "connected," "coupled," or "linked" to another component, it may include not only the component being directly connected, coupled, or connected to another component, but also the component being "connected," "coupled," or "linked" to another component with still another component therebetween.

In addition, when a component is described as being formed or disposed "on (above) or under (below)" of another component, the term on (above) or below (under) includes not only when the two components are in direct contact with each other, but also when one or more other components are formed or disposed between the two components. In addition, when a component is described as being "on (above) or below (under)," the description may include the meanings of an upward direction and a downward direction based on one component.

Figure 1:
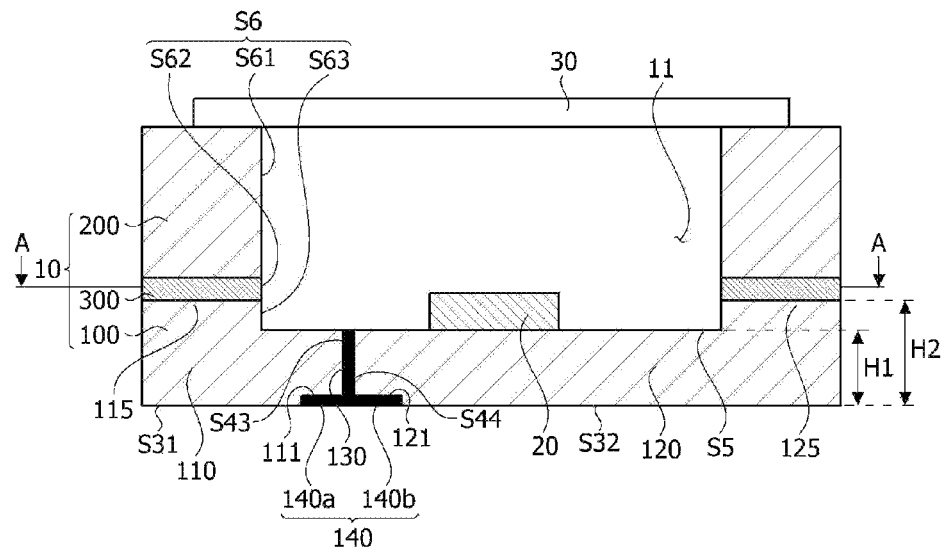
FIG. 1 is a cross-sectional view illustrating a light-emitting element package according to one embodiment of the present invention.
Figure 2:
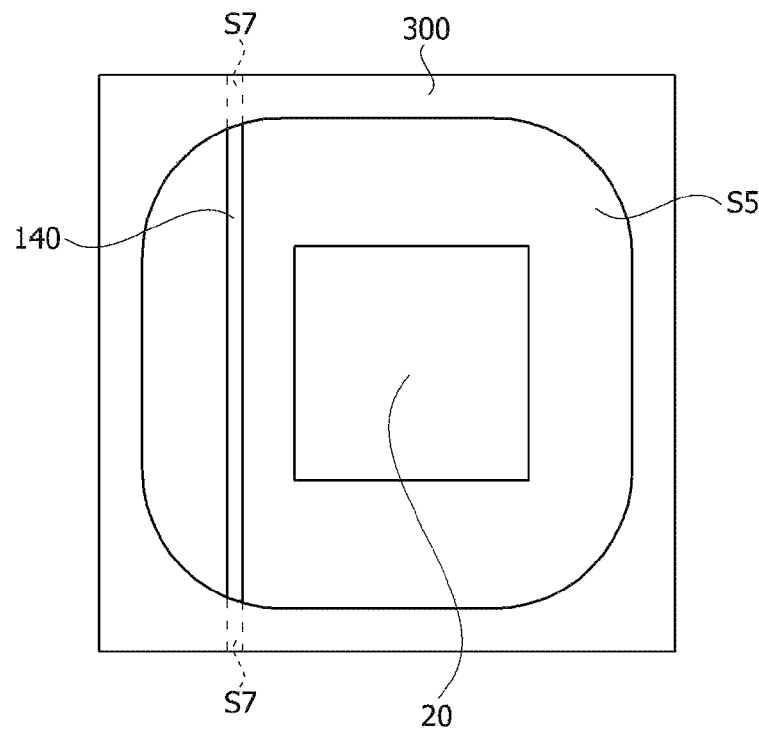
FIG. 2 is a cross-sectional view taken along line A-A of FIG. 1.

FIG. 1 is a cross-sectional view illustrating a light-emitting element package according to one embodiment of the present invention, and FIG. 2 is a cross-sectional view taken along line A-A of FIG. 1.

Referring to FIG. 1, the light-emitting element package according to one embodiment of the present invention may include a body 10, a light-emitting element 20, and a light-transmitting member 30.

The body 10 may include a cavity 11.

The cavity 11 may include an air gap.

The air gap may mean a space filled with air, and one air gap may be formed in an entire area of the cavity 11.

However, the present invention is not necessarily limited thereto, and the cavity 11 may be filled with various gases (e.g., nitrogen gas and the like) in addition to the air and may be filled with a polymer resin or the like.

A lateral surface S6 of the cavity 11 may be disposed perpendicular to a bottom surface S5 thereof, but the present invention is not necessarily limited thereto, and the lateral surface S6 may be disposed to be inclined at an angle that is greater than 90 degrees with respect to the bottom surface S5.

The body 10 may include a lower body 100, an upper body 200, and a first insulating layer 300.

The lower body 100 may include the bottom surface S5 of the cavity 11 and a portion S61 of the lateral surface of the cavity 11, and the upper body 200 may include another portion S63 of the lateral surface of the cavity 11.

The lower body 100 may include a first conductive body 110, a second conductive body 120, and a second insulating layer 130.

Since the first conductive body 110 and the second conductive body 120 have conductivity, the first conductive body 110 and the second conductive body 120 have an advantage in that lead frames can be omitted.

Each of the first conductive body 110 and the second conductive body 120 may be made of a metal. When the first conductive body 110 and the second conductive body 120 contain aluminum (Al), the first conductive body 110 and the second conductive body 120 may each have excellent thermal conductivity ranging from 140 W/m·k to 160 W/m·k.

The second insulating layer 130 may insulate the first conductive body 110 from the second conductive body 120. The second insulating layer 130 may be disposed between the first conductive body 110 and the second conductive body 120. An upper surface of the second insulating layer 130 may be disposed coplanar with the bottom surface of the cavity 11. A lower surface of the second insulating layer 130 may be disposed coplanar with lower surfaces of the first conductive body 110 and the second conductive body 120.

The second insulating layer 130 may be made of an insulating material. For example, the second insulating layer 130 may include a polyimide (PI)-based adhesive material. Thus, the second insulating layer 130 may contain a material having heat resistance that is greater than that of the first insulating layer 300.

In this case, even in a high-temperature and high-pressure environment formed when the second insulating layer 130 is formed or even in a high-temperature environment at a temperature of about 320° C. formed during a die bonding process using eutectic paste or silver (Ag) paste, breakages or cracks of the second insulating layer 130 may be suppressed.

However, the present invention is not necessarily limited thereto, and the second insulating layer 130 may include ethyl-methylene carbonate (EMC), white silicone, photoimageable solder resist (PSR), a silicone resin composition, a modified epoxy resin composition such as silicone-modified epoxy resin, modified silicone resin composition such as epoxy modified silicone resin, polypthalamide (PPA), polycarbonate resin, polyphenylene sulfide (PPS), a liquid crystal polymer (LCP), acrylonitrile-butadiene-styrene (ABS) resin, phenol resin, polybutylene terephthalate (PBT) resin, and the like.

The lower body 100 may include a first insulating portion 140.

The first insulating portion 140 may include a first-first insulating portion 140a disposed in a first groove 111 and a first-second insulating portion 140b disposed in a second groove 121. The first-first insulating portion 140a may be integrally formed with the first-second insulating portion 140b.

The first groove 111 may be disposed in a corner at which a lower surface S31 of the first conductive body 110 is connected to a surface S43 thereof facing the second conductive body 120. The second groove 121 may be disposed in a corner at which a lower surface S32 of the second conductive body 120 is connected to a surface S44 thereof facing the first conductive body 1100. The first groove 111 may be entirely disposed along the corner at which the lower surface S31 of the first conductive body 110 is connected to the surface S43 thereof facing the second conductive body 120. The second groove 121 may be entirely disposed along the corner at which the lower surface S32 of the second conductive body 120 is connected to the surface S44 thereof facing the first conductive body 110.

Inner surfaces of the first groove 111 and the second groove 121 may each have roughness (not shown). This is because, when the inner surfaces of the first groove 111 and the second groove 121 are smooth, adhesive strength with the first insulating portion 140 may become weak. Thus, in order to fix the first insulating portion 140, the inner surfaces of the first groove 111 and the second groove 121 may each have roughness through surface treatment.

The first insulating portion 140 may be made of an insulating material.

For example, the first insulating portion 140 may contain PSR.

The PSR may be green PSR or black PSR. The green PSR may have flexibility that is higher than flexibility of the black PSR and may have less breakage due to a dicing blade during package cutting.

However, the present invention is not necessarily limited thereto, and the first insulating portion 140 may include EMC, white silicone, a silicone resin composition, a modified epoxy resin composition such as silicone-modified epoxy resin, a modified silicone resin composition such as epoxy-modified silicone resin, a PI resin composition, a modified polyimide resin composition, PPA, polycarbonate resin, PPS, a LCP, ABS resin, phenol resin, PBT resin, and the like.

The first insulating portion 140 may suppress occurrence of a short circuit between the first conductive body 110 and the second conductive body 120 due to a soldering defect or the like when the light-emitting element package is mounted.

The upper body 200 may be made of a conductive material, but the present invention is not necessarily limited thereto, and the upper body 200 may be made of a non-conductive material. When the upper body 200 contains a conductive material, particularly Al, the upper body 200 has an advantage of exhibiting high reflectivity in an ultraviolet wavelength band so that a reflective member may be omitted.

The first insulating layer 300 may be disposed between the lower body 100 and the upper body 200.

An inner surface of the first insulating layer 300 may be disposed coplanar with inner surfaces of the lower body 100 and the upper body 200. An outer surface of the first insulating layer 300 may be disposed coplanar with outer surfaces of the lower body 100 and the upper body 200.

The first insulating layer 300 may be made of an insulating material.

For example, the first insulating layer 300 may contain an acrylic-based adhesive material.

Unlike the second insulating layer 130, this is because the first insulating layer 300 is formed in a low-temperature and low-pressure environment.

Like the second insulating layer 130, when the first insulating layer 300 is formed in a high-temperature and high-pressure environment, defects may occur in the process of bonding the first insulating layer 300 to a relatively large area, and breakages or cracks may occur in a prior formed second insulating layer 130 due to the high-temperature and high-pressure environment.

However, the present invention is not necessarily limited thereto, and the first insulating layer 300 may include EMC, white silicone, PSR, a silicone resin composition, a modified epoxy resin composition such as silicone-modified epoxy resin, a modified silicone resin composition such as epoxy-modified silicone resin, a PI resin composition, a modified PI resin composition, PPA, polycarbonate resin, PPS, a LCP, ABS resin, phenol resin, PBT resin, and the like.

When compared with the second insulating layer 130, a thermal dissipation characteristic, for example, thermal conductivity, is a relatively unimportant factor in material selection, and thus the first insulating layer 300 may be made of a material having thermal conductivity that is lower than thermal conductivity of the second insulating layer 130 so that a wide variety of material choices may be made.

The light-emitting element 20 may be disposed on the bottom surface of the cavity 11.

A sub-mount is disposed on the bottom surface of the cavity 11 and the light-emitting element 20 may be disposed on the sub-mount, but the present invention is not limited thereto, and the light-emitting element 20 may be disposed on the bottom surface of the cavity 11 without the sub-mount.

The light-emitting element 20 may be electrically connected to the first conductive body 110 and the second conductive body 120.

The light-emitting element 20 may emit ultraviolet rays. For example, the light-emitting element 20 may emit light in a near ultraviolet wavelength band having a peak wavelength ranging from 320 nm to 420 nm (UV-A), light in a far ultraviolet wavelength band having a peak wavelength ranging from 280 nm to 320 nm (UV-B), and light in a deep ultraviolet wavelength band having a peak wavelength ranging from 100 nm to 280 nm (UV-C).

The light-transmitting member 30 may be disposed on the upper body 200.

The light-transmitting member 30 may be made of a material having excellent transmittance of ultraviolet rays, for example, quartz, but the present invention is not limited thereto.

A height H1 from the lower surface of the lower body 100 to the bottom surface of the cavity 11 may be smaller than a height H2 from the lower surface of the lower body 100 to a lower surface of the first insulating layer 300.

Thus, the first conductive body 110 may include a first side wall 115 which further protrudes toward the upper body 200 than the bottom surface S5 of the cavity 11, the second conductive body 120 may have a second side wall 125 which further protrudes toward the upper body 200 than the bottom surface S5 of the cavity 11, and the first insulating layer 300 may be disposed on the first side wall 115 and the second side wall 125.

In addition, an inner surface S61 of the first or second side wall 115 or 125 may be coplanar with and connected to an inner surface S62 of the first insulating layer 300, and the inner surface S62 of the first insulating layer 300 may be coplanar with and connected to an inner surface S63 of the upper body 200. That is, the lateral surface S6 of the cavity 11 may extend without a step at upper and lower ends of the first insulating layer 300.

A ratio of the height H2 from the lower surface of the lower body 100 to the lower surface of the first insulating layer 300 to the height H1 from the lower surface of the lower body 100 to the bottom surface of the cavity 11 may range from 1.09:1 to 1.72:1.

When the height ratio is 1.09:1 or higher, even when foreign materials infiltrate into the cavity 11 during a package manufacturing process, a gap between the lower body 100 and the upper body 200 is secured so that insulating therebetween may be improved.

When the height ratio is 1.72:1 or less, light absorption due to the first insulating layer 300, which may be increased according to a height of the first insulating layer 300, is suppressed within an allowable range so that light efficiency may be improved. Since an amount of light directly incident on the first insulating layer 300 may be decreased, cracks and the like of the first insulating layer 300 due to the light may be prevented. In addition, it is possible to improve insulation and a bonding force between the lower body 100 and the upper body 200.

However, the present invention is not necessarily limited thereto, and the height H1 from the lower surface of the lower body 100 to the bottom surface of the cavity 11 may be equal to the height H2 from the lower surface of the lower body 100 to the lower surface of the first insulating layer 300.

Referring to FIG. 2, the lower surface and the first insulating layer 300 may be disposed to surround the bottom surface S5 of the cavity.

A portion S7 of the lower surface of the first insulating layer 300 may be in contact with the second insulating layer 140.

Hereinafter, a light-emitting element package according to another embodiment of the present invention will be described. Even when not described in the present embodiment, the items already described in other embodiments of the present specification may be considered to be included in the present embodiment unless a description is opposite or contradictory to the items.

Figure 3:
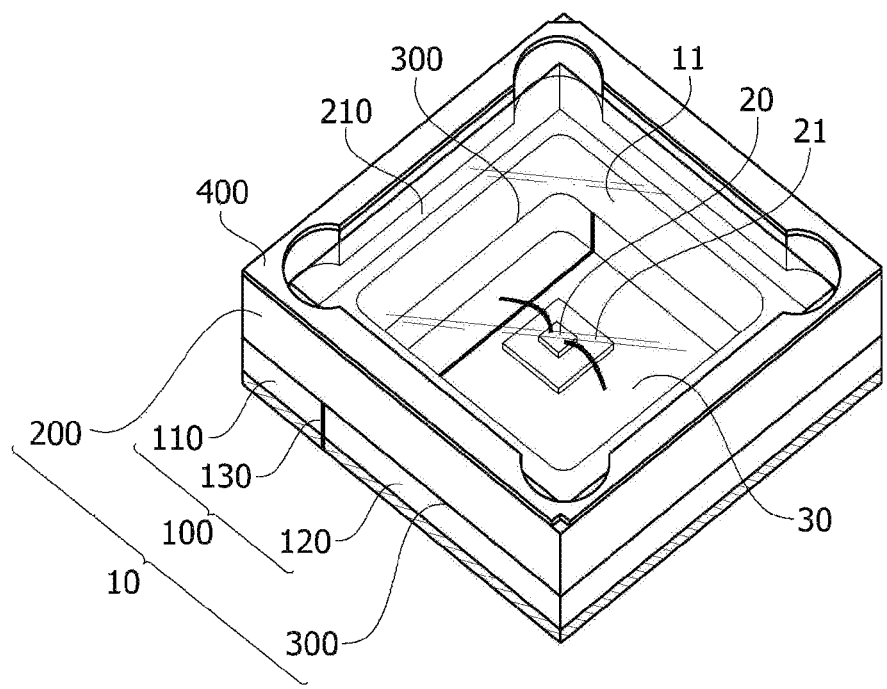
FIG. 3 is a conceptual diagram illustrating a light-emitting element package according to another embodiment of the present invention.
Figure 4:
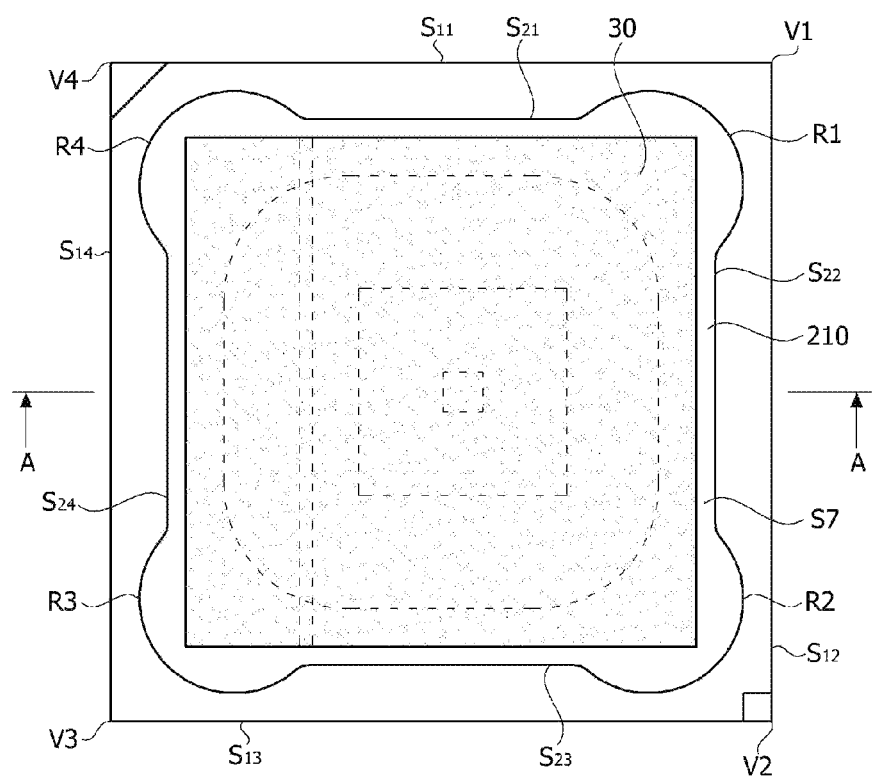
FIG. 4 is a plan view of FIG. 3.
Figure 5:
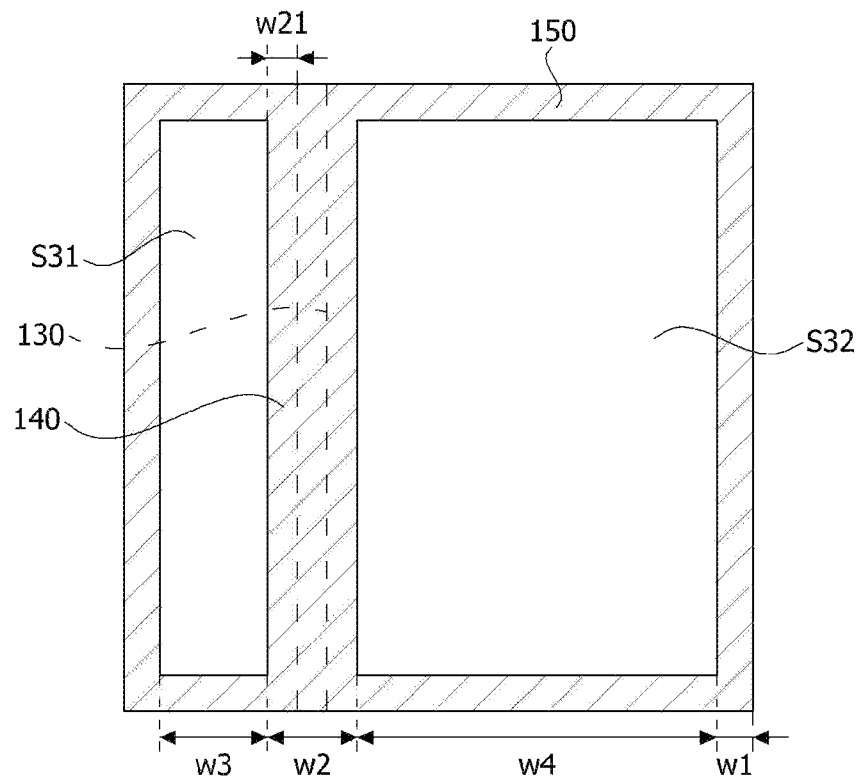
FIG. 5 is a bottom view of FIG. 3.
Figure 6:
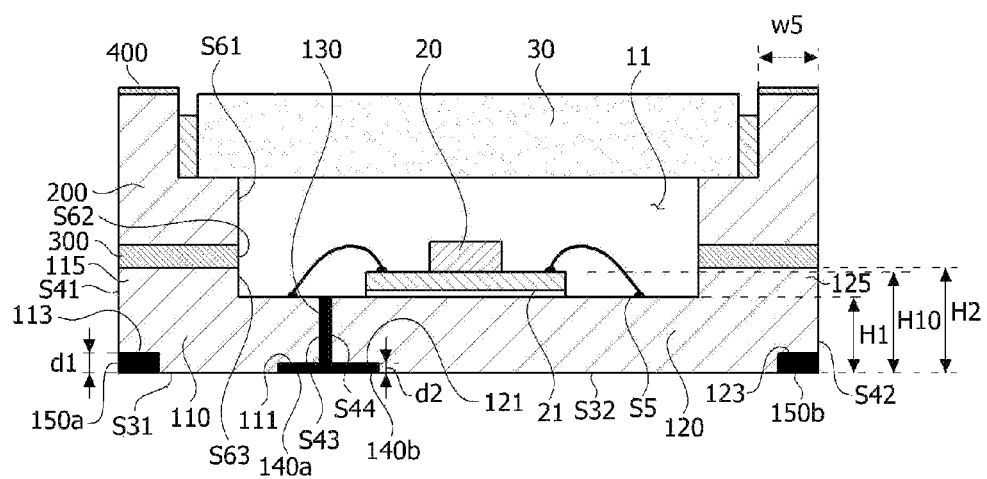
FIG. 6 is a cross-sectional view taken along line A-A of FIG. 3.

FIG. 3 is a conceptual diagram illustrating a light-emitting element package according to another embodiment of the present invention, FIG. 4 is a plan view of FIG. 3, FIG. 5 is a bottom view of FIG. 3, and FIG. 6 is a cross-sectional view taken along line A-A of FIG. 3.

Referring to FIGS. 3 and 4, an upper body 200 may include a stepped portion 210.

The stepped portion 210 may be disposed in an upper portion of a cavity 11. The stepped portion 210 may be formed to extend from an inner surface of the upper body 200 toward an outer surface thereof or may be formed to extend from an upper surface of the upper body 200 toward a lower surface thereof.

A third insulating layer 400 may be disposed on the upper body 200.

When the third insulating layer 400 is present, it is possible to suppress occurrence of burrs in corners of an upper portion of a body 10 during package cutting.

However, the present invention is not necessarily limited thereto, and the third insulating layer 400 may be omitted.

When the third insulating layer 400 is omitted, it is possible to reduce yield degradation due to breakage of the third insulating layer 400 during package cutting.

The third insulating layer 400 may be made of an insulating material.

For example, the third insulating layer 400 may contain PSR.

The PSR may be green PSR or black PSR. The green PSR may have flexibility that is higher than flexibility of the black PSR and may have less breakage due to a dicing blade during package cutting.

However, the present invention is not necessarily limited thereto, and the third insulating layer 400 may include EMC, white silicone, a silicone resin composition, a modified epoxy resin composition such as silicone-modified epoxy resin, a modified silicone resin composition such as epoxy-modified silicone resin, a PI resin composition, a modified polyimide resin composition, PPA, polycarbonate resin, PPS, a LCP, ABS resin, phenol resin, PBT resin, and the like.

A light-transmitting member 30 may be disposed on a bottom surface S7 of the stepped portion 210 so that a lower surface of the light-transmitting member 30 may be disposed at a lower level than the upper surface of the upper body 200.

Referring to FIG. 4, the upper body 200 may include a first outer surface S11 and a third outer surface S13 which are opposite to each other, a second outer surface S12 and a fourth outer surface S14 which are opposite to each other, a first corner V1 at which the first outer surface S11 is connected to the second outer surface S12, a second corner V2 at which the second outer surface S12 is connected to the third outer surface S13, a third corner V3 at which the third outer surface S13 is connected to the fourth outer surface S14, and a fourth corner V4 at which the fourth outer surface S14 is connected to the first outer surface S11. The stepped portion 210 may include a first lateral surface S21 and a third lateral surface S23 which face each other, a second lateral surface S22 and a fourth lateral surface S24 which face each other, a first recess R1 disposed in a corner at which the first lateral surface S21 is connected to the second lateral surface S22, a second recess R2 disposed in a corner at which the second lateral surface S22 is connected to the third lateral surface S23, a third recess R3 disposed in a corner at which the third lateral surface S23 is connected to the fourth lateral surface S24, and a fourth recess R4 disposed in a corner at which the fourth lateral surface S24 is connected to the first lateral surface S21.

The first recess R1 may be formed to extend toward the first corner V1, the second recess R2 may be formed to extend toward the second corner V2, the third recess R3 may be formed to extend toward the third corner V3, and the fourth recess R4 may be formed to extend toward the fourth corner V4. The first to fourth recesses R1, R2, R3, and R4 may each have a curvature.

When the light-transmitting member 30 has a quadrangular shape in which a corner has no curvature, the first to fourth recesses R1, R2, R3, and R4 allow the light-transmitting member 30 to be inserted into the stepped portion 210 even when the light-transmitting member 30 is rotated to some extent.

The stepped portion 210 may have a quadrangular shape with the four lateral surfaces S21, S22, S23, and S24, but the present invention is not necessarily limited thereto, and the stepped portion 210 may have a polygonal shape in addition to the quadrangular shape.

Referring to FIGS. 5 and 6, a lower body 100 may include a second insulating portion 150.

The second insulating portion 150 may include a second-first insulating portion 150a disposed in a third groove 113 and a second-second insulating portion 150b disposed in a fourth groove 123. The second-first insulating portion 150a may be integrally formed with the second-second insulating portion 150b.

The third groove 113 may be disposed in a corner at which a lower surface S31 of a first conductive body 110 is connected to an outer surface S41 thereof. The fourth groove 123 may be disposed in a corner at which a lower surface S32 of a second conductive body 120 is connected to an outer surface S42 thereof. The third groove 113 may be entirely disposed along the corner at which the lower surface S31 of the first conductive body 110 is connected to the outer surface S41 thereof. The fourth groove 123 may be entirely disposed along the corner at which the lower surface S32 of the second conductive body 120 is connected to the outer surface S42 thereof.

Inner surfaces of the third groove 113 and the fourth groove 123 may each have roughness (not shown). This is because, when the inner surfaces of the third groove 113 and the fourth groove 123 are smooth, adhesive strength with the second insulating portion 150 may become weak. Thus, in order to fix the second insulating portion 150, the inner surfaces of the third groove 113 and the fourth groove 123 may each have roughness through surface treatment.

The second insulating portion 150 may be made of an insulating material.

For example, the second insulating portion 150 may contain PSR.

The PSR may be green PSR or black PSR. The green PSR may have flexibility that is higher than flexibility of the black PSR and may have less breakage due to a dicing blade during package cutting.

However, the present invention is not necessarily limited thereto, and the second insulating portion 150 may include EMC, white silicone, a silicone resin composition, a modified epoxy resin composition such as silicone-modified epoxy resin, a modified silicone resin composition such as epoxy-modified silicone resin, a PI resin composition, a modified polyimide resin composition, PPA, polycarbonate resin, PPS, a LCP, ABS resin, phenol resin, PBT resin, and the like.

The second insulating portion 150 may suppress occurrence of burrs in corners of a lower portion of a body 10 during package cutting.

When each of the first conductive body 110 and the second conductive body 120 is made of a metal material such as Al, burrs may occur in the corners during package cutting. However, when the second insulating portion 150 is made of an insulating material, it is possible to suppress occurrence of the burrs in the corners during package cutting. When burrs occur in the corners of the lower portion of the body 10, the lower surface of the body 10 becomes uneven so that mounting of the body 10 on a substrate may become unstable, and a thickness of the body 10 becomes non-uniform such that some areas of the body 10 are lifted so that a measurement error may occur.

The description on the second insulating portion 150 may be considered to be included in that of one embodiment.

A sub-mount 21 may be made of silicon (Si).

A width of the sub-mount 21 may range from 1000 μm to 1200 μm and, preferably, may be 1100 μm in a horizontal or vertical direction. A thickness of the sub-mount 21 may range from 190 μm to 210 μm and, preferably, may be 200 μm.

A ratio of a height H2 from a lower surface of the lower body 100 to a lower surface of the first insulating layer 300 to a height H10 from the lower surface of the lower body 100 to an upper surface of the sub-mount 21 may range from 1.05:1 to 1.63:1.

When the height ratio is 1.05:1 or higher, even when foreign materials infiltrate into the cavity 11 during a package manufacturing process, a gap between the lower body 100 and the upper body 200 is secured so that insulating may be improved.

When the height ratio is 1.63:1 or less, light absorption due to the first insulating layer 300, which may be increased according to a height of the first insulating layer 300, is suppressed within an allowable range so that light efficiency may be improved. In addition, since an amount of light directly incident on the first insulating layer 300 may be decreased, cracks and the like of the first insulating layer 300 due to the light may be prevented. In addition, it is possible to improve insulation and a bonding force between the lower body 100 and the upper body 200.

A thickness d1 of the second insulating portion 150 in a first direction (Y direction) may range from 50 μm to 150 μm. The first direction (Y direction) may be a direction from the lower surface of the body 10 to an upper surface thereof. When the thickness is 50 μm or more, a sufficient thickness may be secured so that occurrence of burrs may be prevented during package cutting. When the thickness is 150 μm or less, the second insulating portion 150 may be prevented from protruding from the lower surfaces S31 and S32 of the body 10.

A width w1 of the second insulating portion 150 in a second direction (X direction) may range from 100 μm to 300 μm. The second direction (X direction) may be a direction perpendicular to the first direction. When the width is 100 μm or more, the second insulating portion 150 may be sufficiently fixed to the third groove 113 and the fourth groove 123. When the width is 300 μm or less, areas in which electrodes are mounted on the lower surfaces S31 and S32 of the body 10 may be secured.

According to an embodiment, a ratio of the thickness to the width (d1:w1) of the second insulating portion 150 may range from 1:1.5 to 1:6. That is, the width of the second insulating portion 150 may be greater than the thickness thereof. When the thickness-to-width ratio is satisfied, the second insulating portion 150 is sufficiently fixed to the third groove 113 and the fourth groove 123 so that occurrence of burrs may be suppressed.

A thickness d2 of the first insulating portion 140 in the first direction (Y direction) may range from 10 μm to 100 μm. When the thickness is 10 μm or more, the first insulating portion 140 may be sufficiently fixed to a first groove 111 and a second groove 121. When the thickness is 100 μm or less, a depth of each of the first groove 111 and the second groove 121 may be controlled to be small so that a thickness of an area in which the light-emitting element 20 is mounted may be secured. Since the area in which the light-emitting element 20 is mounted is an area having the smallest thickness in the body 10 due to formation of a cavity 11, it may be advantageous to form each of the first groove 111 and the second groove 121 to have a depth which is as shallow as possible.

A width w2 of the first insulating portion 140 in the second direction (X direction) may range from 300 μm to 700 μm and, preferably, from 450 μm to 550 μm. When the width is 300 μm or more, the lower surfaces S31 and S32 of the first and second conductive bodies 110 and 120 are sufficiently spaced apart from each other so that a short circuit may be prevented. When the width is 700 μm or less, it is possible to secure sufficient areas in which the electrodes are mounted on the lower surfaces S31 and S32 of the body 10. In addition, when the width w2 of the first insulating portion 140 in the second direction (X direction) ranges from 450 μm to 550 μm, occurrence of burrs may be prevented in an inner corner among the corners of the first conductive body 110 and the second conductive body 120, which is in contact with a position at which the second insulating layer 130 and the second insulating portion 150 meet, and, simultaneously, insulation between the first conductive body 110 and the second conductive body 120 may be secured when the substrate is mounted. Consequently, the width w2 of the first insulating portion 140 may be greater than the width w1 of the second insulating portion 150.

The thickness d1 of the second insulating portion 150 may be greater than the thickness d2 of the first insulating portion 140. Since the area in which the light-emitting element 20 is mounted is an area having the smallest thickness in the body 10 due to formation of a cavity 11, it may be advantageous to form each of the first groove 111 and the second groove 121 to have a depth which is as shallow as possible. In addition, in order to prevent occurrence of burrs, the second insulating portion 150 may have a predetermined thickness. As a result, when the thickness d1 of the second insulating portion 150 is greater than the thickness d2 of the first insulating portion 140, the occurrence of burrs may be effectively prevented, and strength of a package may be secured.

However, the present invention is not limited thereto, and the thickness d1 of the second insulating portion 150 may be equal to the thickness d2 of the first insulating portion 140.

The lower surface S32 of the second conductive body 120 may be wider than the lower surface S31 of the first conductive body 110. An area ratio (w4:w3) of the lower surface S32 of the second conductive body 120 to the lower surface S31 of the first conductive body 110 may range from 1:0.2 to 1:0.6. When the area ratio is 1:0.2 or more, an area of the lower surface S31 of the first conductive body 110 is secured so that a short circuit may be prevented. When the area ratio is 1:0.6 or less, a space in which the sub-mount is to be disposed on an upper portion of the lower surface S32 of the second conductive body 120 may be secured.

A ratio (w1:w4) of the width w1 of the lower surface of the third groove to the width w4 of the lower surface of the second conductive body may range from 1:3 to 1:5. When a width ratio is 1:3 or more, an area of the lower surface S32 of the second conductive body is increased so that an area in which the sub-mount is to be mounted may be secured. When the width ratio is 1:5 or less, the width of the second insulating portion 150 is increased so that the occurrence of burrs may be effectively suppressed.

A ratio (w21:w4) of a width w21 of the lower surface of the first groove to the width w1 of the lower surface of the third groove may range from 1:0.8 to 1:1.2. That is, the width w2 of the first insulating portion 140 may be two or more times the width w1 of the second insulating portion 150. Consequently, the lower surfaces S31 and S32 of the first conductive body and the second conductive body are sufficiently spaced apart from each other so that a short circuit may be prevented.

The width w1 of the second insulating portion 150 may be smaller than a width w5 of the upper surface of the body. The width w1 of the second insulating portion 150 may be 50% to 90% of the width w5 of the upper surface of the body. Owing to the above structure, an area for mounting the electrode is sufficiently secured in the lower surface of the body 10, and the width of the second insulating portion 150 is secured so that adhesive strength with the body 10 may be secured.

Figure 7:
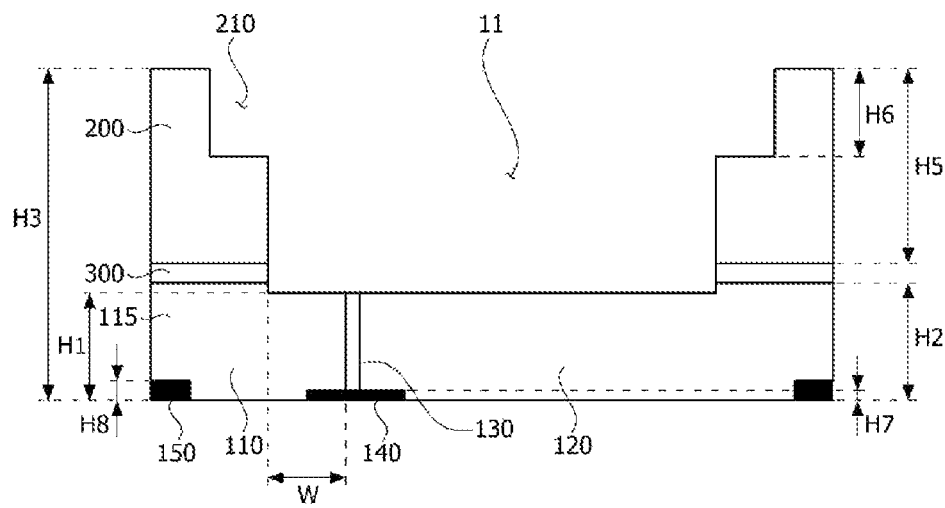
FIG. 7 is a modified example of a body shown in FIG. 6.

FIG. 7 is a modified example of the body shown in FIG. 6.

Referring to FIG. 7, the height H1 from the lower surface of the lower body 100 to the bottom surface of the cavity 11 may range from 0.35 mm to 0.55 mm.

The height H2 from the lower surface of the lower body 100 to the lower surface of the first insulating layer 300 may range from 0.5 mm to 0.7 mm and, preferably, may be 0.6 mm.

A height H3 from the lower surface of the lower body 100 to the upper surface of the upper body 200 may range from 1.3 mm to 1.7 mm.

A height H5 from the upper surface of the first insulating layer 300 to the upper surface of the upper body 200 may range from 0.6 mm to 1.0 mm.

A height H6 from a lower surface of the stepped portion 210 to the upper surface of the upper body 200 may range from 0.35 mm to 0.55 mm.

A height H7 or d2 from the lower surface of the first insulating portion 140 to the upper surface thereof may range from 0.04 mm to 0.06 mm and, preferably, may be 0.05 mm.

A height H8 or d1 from the lower surface of the second insulating portion 150 to the upper surface thereof may range from 0.09 mm to 0.11 mm and, preferably, may be 0.1 mm.

A width W from an inner surface of the first side wall 115 to a surface of the second insulating layer 130 in contact with the first conductive body 110 may range from 0.3 mm to 0.6 mm and, preferably, may be 0.4 mm.

Table 1 below shows various modified examples of the body 10 in specific values (unit: mm).

TABLE 1

|    | First example | Second example | Third example | Fourth example | Fifth example | Sixth example |
|----|---------------|----------------|---------------|----------------|---------------|---------------|
| H1 | 0.35          | 0.35           | 0.35          | 0.45           | 0.55          | 0.55          |
| H2 | 0.6           | 0.6            | 0.6           | 0.6            | 0.6           | 0.6           |
| H3 | 1.3           | 1.3            | 1.5           | 1.5            | 1.7           | 1.7           |
| H5 | 0.6           | 0.6            | 0.8           | 0.8            | 1             | 1             |
| H6 | 0.35          | 0.45           | 0.55          | 0.45           | 0.45          | 0.55          |
| H7 | 0.05          | 0.05           | 0.05          | 0.05           | 0.05          | 0.05          |
| H8 | 0.1           | 0.1            | 0.1           | 0.1            | 0.1           | 0.1           |
| W  | 0.4           | 0.4            | 0.4           | 0.4            | 0.4           | 0.4           |

Hereinafter, a manufacturing process of the light-emitting element package according to the present invention will be described.

FIGS. 8 to 13 are diagrams illustrating a manufacturing process of the light-emitting element package according to the present invention.

Figure 8:
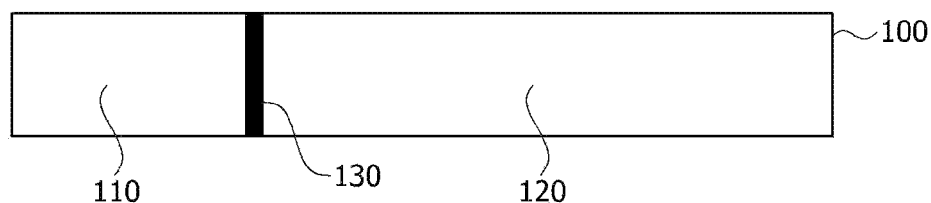
FIGS. 8 to 13 are diagrams illustrating a manufacturing process of the light-emitting element package according to the present invention.

Referring to FIG. 8, the lower body 100 may be manufactured such that the second insulating layer 130 is disposed between the first conductive body 110 and the second conductive body 120.

Figure 9:
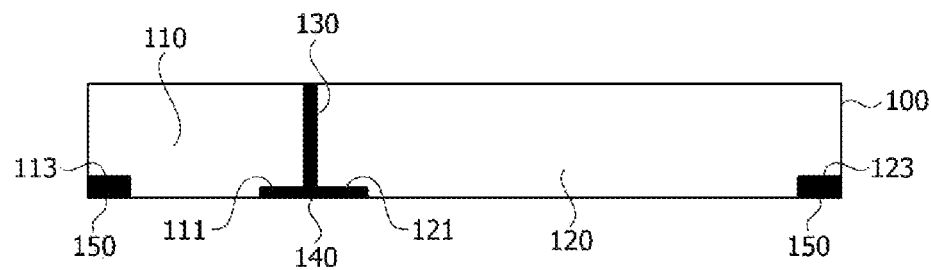

Referring to FIG. 9, the first groove 111 to the fourth groove 123 may be formed in the lower body 100, and then the first insulating portion 140 and the second insulating portion 150 may be disposed in the first groove 111 to the fourth groove 123.

However, the present invention is not necessarily limited thereto, and the third groove 113, the fourth groove 123, and the second insulating portion 150 may be omitted.

Figure 10:
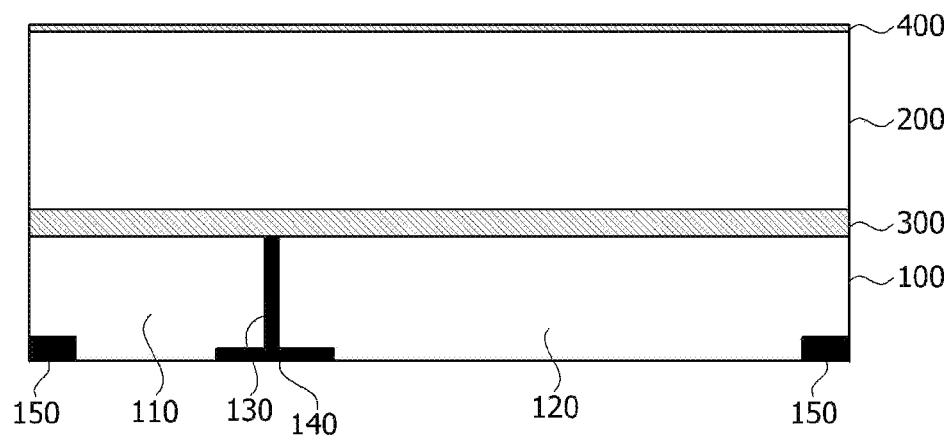

Referring to FIG. 10, the first insulating layer 300, the upper body 200, and the third insulating layer 400 may be stacked on the lower body 100.

However, the present is not necessarily limited thereto, and the third insulating layer 400 may be omitted.

Figure 11:
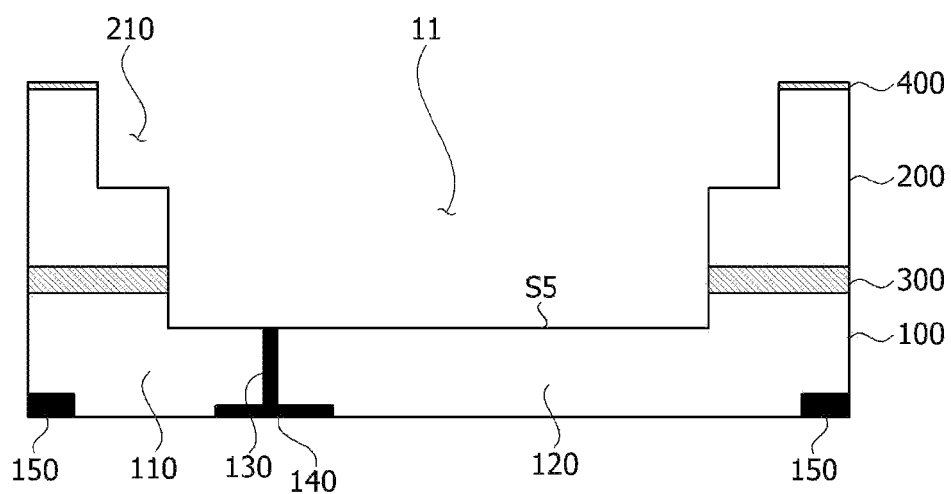

Referring to FIG. 11, the cavity 11 may be formed such that the bottom surface S5 of the cavity 11 is included in the lower body 100. In this case, the stepped portion 210 may be disposed in the upper portion of the cavity 11.

However, the present is not necessarily limited thereto, and the stepped portion 210 may be omitted.

Figure 12:
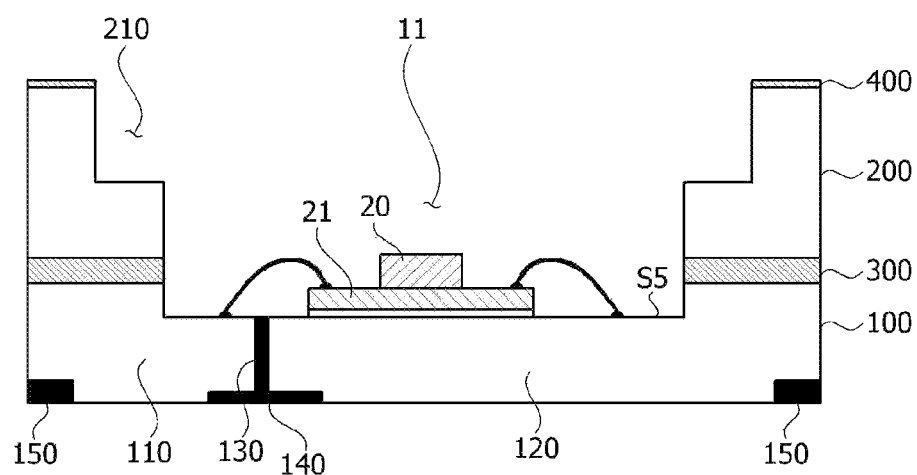

Referring to FIG. 12, the light-emitting element 20 may be disposed on the bottom surface S5 of the cavity 11 and may be electrically connected to the first conductive body 110 and the second conductive body 120. In this case, the sub-mount 21 may be disposed between the bottom surface S5 of the cavity 11 and the light-emitting element 20.

However, the present is not necessarily limited thereto, and the sub-mount 21 may be omitted.

Figure 13:
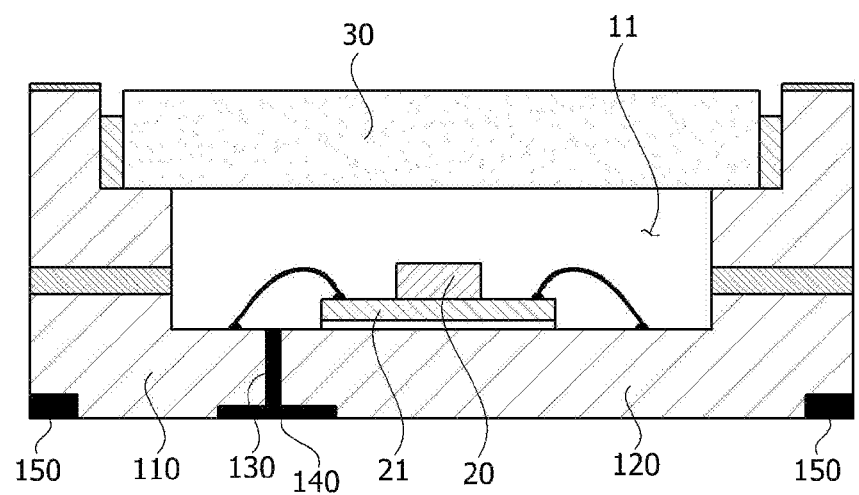

Referring to FIG. 13, the light-transmitting member 30 may be inserted into the stepped portion 210. However, the present invention is not necessarily limited thereto, and, when the stepped portion 210 is omitted, the light-transmitting member 30 may be disposed on the upper body 200.

Hereinafter, a light-emitting element package according to still another embodiment of the present invention will be described. Even when not described in the present embodiment, the items already described in other embodiments of the present specification may be considered to be included in the present embodiment unless a description is opposite or contradictory to the items.

Figure 14:
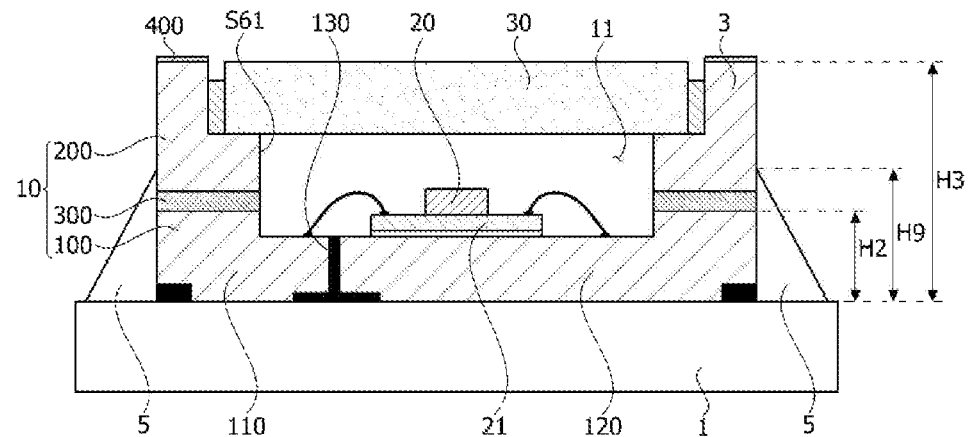
FIG. 14 is a cross-sectional view illustrating a light-emitting element module according to still another embodiment of the present invention.

FIG. 14 is a cross-sectional view illustrating a light-emitting element module according to still another embodiment of the present invention.

Referring to FIG. 14, the light-emitting element module according to still another embodiment of the present invention may include a substrate 1, a light-emitting element package 3, and a sealing member 5.

The substrate 1 may be a circuit substrate on which the light-emitting element package 3 is mounted. The substrate 1 may include a first pad (not shown) and a second pad (not shown) to which a first conductive body 110 and a second conductive body 120 of the light-emitting element package 3 are electrically connected.

The light-emitting element package 3 may be the light-emitting element package according to one embodiment or another embodiment of the present invention.

The sealing member 5 may be in contact with an upper surface of the substrate 1 and a lateral surface of the light-emitting element package 3.

The sealing member 5 may be made of an insulating material.

For example, the sealing member 5 may include a silicone-based waterproof material.

This is because the sealing member 5 should prevent infiltration of water or chemicals falling from an upper portion of the light-emitting element package 3 so that a short circuit between the first conductive body 110 and the second conductive body 120 may be suppressed.

However, the present invention is not necessarily limited thereto, and the sealing member 5 may include EMC, PSR, a modified epoxy resin composition such as silicone-modified epoxy resin, a PI resin composition, a modified PI resin composition, PPA, polycarbonate resin, PPS, an LCP, ABS resin, phenol resin, acrylic resin, PBT resin, and the like.

A height H9 from the upper surface of the substrate 1 to an upper end of a surface of the sealing member 5 in contact with the body 10 may be greater than a height H2 from the upper surface of the substrate 1 to the lower surface of a first insulating layer 300. Consequently, the sealing member 5 may surround an entirety of outer surfaces of a first conductive body 110 and a second conductive body 120 so that, even when water or chemicals fall on the upper portion of the light-emitting element package 3, a short circuit between the first conductive body 110 and the second conductive body 120 may be suppressed.

Meanwhile, since the lower body 100 and the upper body 200 are disposed to be insulated from each other due to the first insulating layer 300, there is no need for the sealing member 5 to surround the entirety of the outer surfaces of the body 10 so as to suppress the short circuit between the first conductive body 110 and the second conductive body 120. That is, there is no need for the sealing member 5 to be filled until the upper end of the surface of the sealing member 5 in contact with the body 10 reaches an upper surface of the upper body 200. Thus, the height H9 from the upper surface of the substrate 1 to the upper end of the surface of the sealing member 5 in contact with the body 10 may be smaller than a height H3 from the upper surface of the substrate 1 to the upper surface of the upper body 200.

Figure 15:
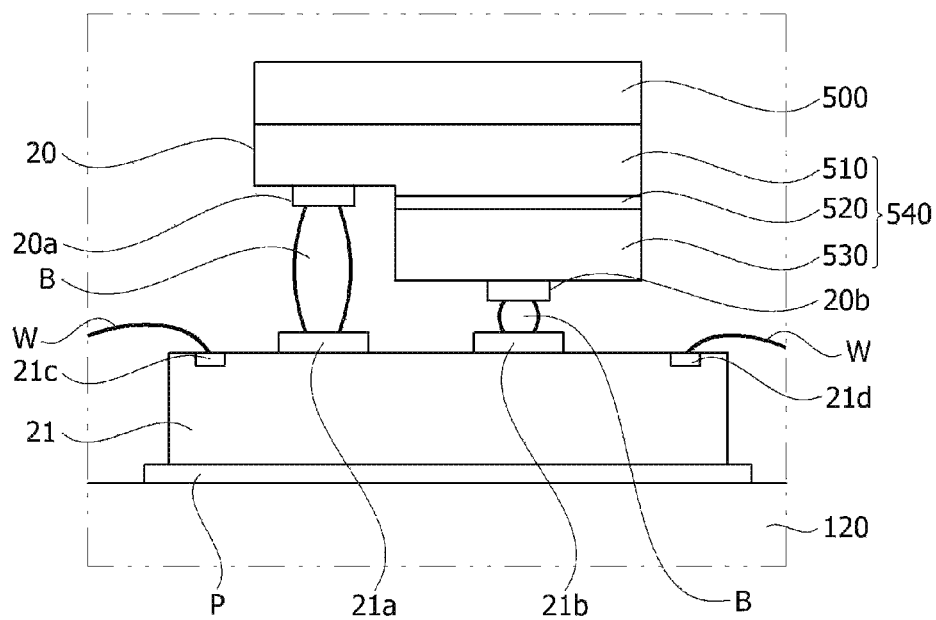
FIG. 15 is a conceptual diagram illustrating a light-emitting element of FIG. 1.

FIG. 15 is a conceptual diagram illustrating the light-emitting element of FIG. 1, and FIGS. 16 to 18 are modified examples of the light-emitting element of FIG. 1.

Referring to FIG. 15, like a flip chip, the light-emitting element 20 may be mounted on the sub-mount 21. That is, a first electrode 20a and a second electrode 20b of the light-emitting element 20 may be mounted on a first pad 21a and a second pad 21b of the sub-mount 21 in the form of a flip chip. Through an Ag bump B, the first electrode 20a may be bonded to the first pad 21a, and the second electrode 20b may be bonded to the second pad 21b.

The first pad 21a may be connected to a third electrode 21c of the sub-mount 21 through a first circuit pattern (not shown). The second pad 21b may be connected to a fourth electrode 21d of the sub-mount 21 through a second circuit pattern (not shown).

The third electrode 21c may be connected to the first conductive body 110 through a first wire W. The fourth electrode 21d may be connected to the second conductive body 120 through a second wire W.

The sub-mount 21 may be bonded to the second conductive body 120 through an Ag paste P.

The light-emitting element 20 may include a substrate 500, a first conductive type semiconductor layer 510, an active layer 520, and a second conductive type semiconductor layer 530. Each semiconductor layer may have an Al composition so as to emit light in an ultraviolet wavelength band.

The substrate 500 includes a conductive substrate or an insulating substrate. The substrate 500 may be a material suitable for a semiconductor material growth or a carrier wafer. The substrate 500 may be formed of a material selected from among $Al_2O_3$, SiC, GaAs, GaN, ZnO, Si, GaP, InP, and Ge, but the present invention is not necessarily limited thereto. The substrate 500 may be omitted, as necessary.

A buffer layer (not shown) may be disposed between the substrate 500 and the first conductive type semiconductor layer 510. The buffer layer may reduce a lattice mismatch between the substrate 500 and a light-emitting structural body 540 provided thereon.

The first conductivity type semiconductor layer 510 may be formed of a compound semiconductor including a group III-V, a group II-VI, or the like and may be doped with a first dopant. For example, the first conductive type semiconductor layer 510 may be selected from among GaN, AlGaN, InGaN, InAlGaN, and the like which are semiconductor materials having a composition formula of $In_{x1}Al_{y1}Ga_{1-x1-y1}N$ ($0 \le x1 \le 1$, $0 \le y1 \le 1$, and $0 \le x1+y1 \le 1$). In addition, the first dopant may be an n-type dopant such as Si, Ge, Sn, Se, or Te. When the first dopant is an n-type dopant, the first conductive type semiconductor layer 510 doped with the first dopant may be an n-type semiconductor layer.

The active layer 520 is a layer in which electrons (or holes) implanted through the first conductive type semiconductor layer 510 and holes (or electrons) implanted through the second conductive type semiconductor layer 530 are recombined. The active layer 520 may be transitioned to a low energy level due to a recombination of electrons and holes to emit light having a wavelength corresponding to the transition.

The active layer 520 may have any one among a single well structure, a multi-well structure, a single quantum well structure, a multi quantum well (MQW) structure, a quantum dot structure, or a quantum wire structure, but the present invention is not necessarily limited thereto.

The second conductivity type semiconductor layer 530 may be formed on the active layer 520, may be formed of a compound semiconductor including a group III-V, a group II-VI, or the like, and may be doped with a second dopant. The second conductive type semiconductor layer 530 may be formed of a semiconductor material having a composition formula of $In_{x5}Al_{y2}Ga_{1-x5-y2}N$ ($0<x5<1$, $0<y2<1$, and $0<x5+y2<1$) or a material selected from among AlInN, AlGaAs, GaP, GaAs, GaAsP, and AlGaInP. When the second dopant is a p-type dopant such as Mg, Zn, Ca, Sr, or Ba, the second conductive type semiconductor layer 530 doped with the second dopant may be a p-type semiconductor layer.

The first electrode 20a may be electrically connected to the first conductive type semiconductor layer 510, and the second electrode 20b may be electrically connected to the second conductive type semiconductor layer 530. Each of the first and second electrodes 20a and 20b is selected from among Ti, Ru, Rh, Ir, Mg, Zn, Al, In, Ta, Pd, Co, Ni, Si, Ge, Ag, Au, and a selective alloy thereof.

As described above, although the light-emitting element 20 has been described as having a flip chip structure disposed on the sub-mount 21, the present invention is not necessarily limited thereto.

Figure 16:
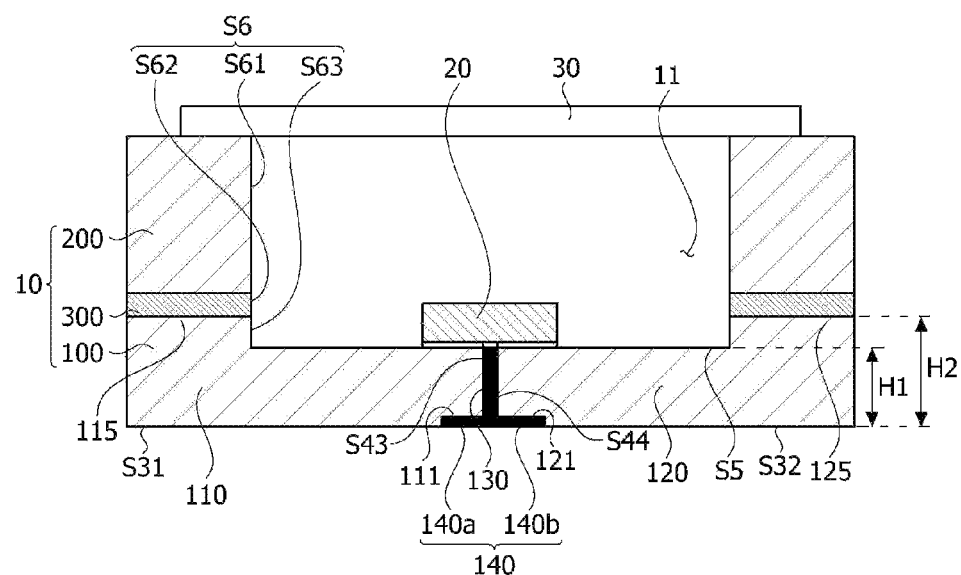
FIGS. 16 to 18 are modified examples of the light-emitting element of FIG. 1.

For example, as shown in FIG. 16, the light-emitting element 20 may have a flip chip structure which is directly mounted on the first conductive body 110 and the second conductive body 120 without a sub-mount.

Figure 17:
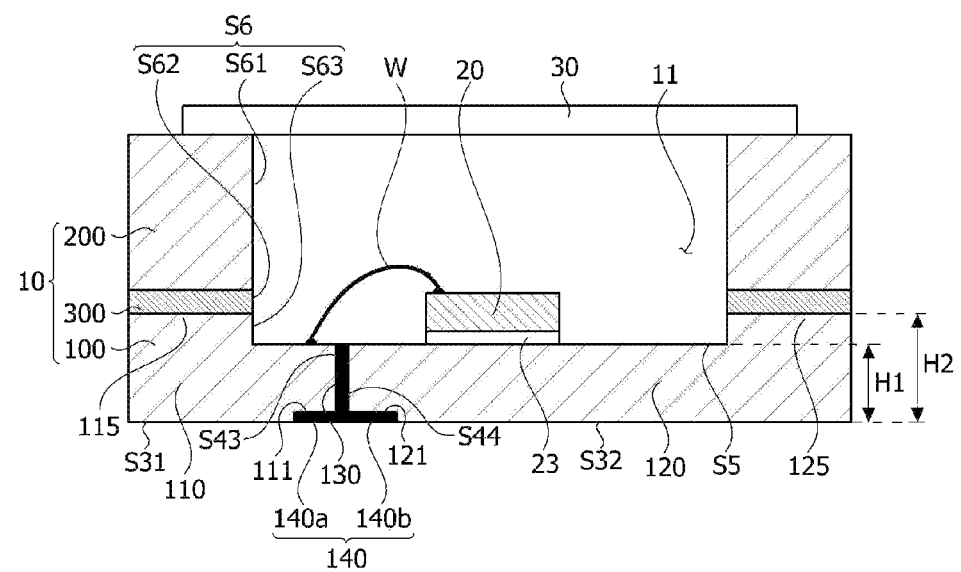

As another example, as shown in FIG. 17, the light-emitting element 20 may have a vertical type structure which is disposed on the second conductive body 120 without a sub-mount and connected to the first conductive body 110 through a wire W.

Figure 18:
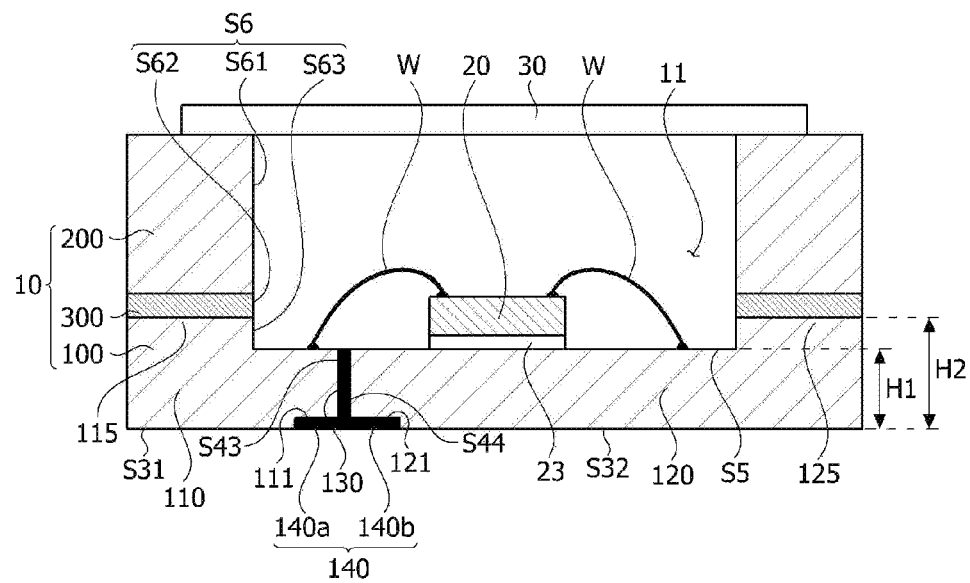

As still another example, as shown in FIG. 18, the light-emitting element 20 may have a horizontal type structure which is disposed on the second conductive body 120 without a sub-mount and connected to the first conductive body 110 and the second conductive body 120 through a wire W.

In FIGS. 17 and 18, a buffer electrode 23 may be disposed on the bottom surface of the cavity 11 and the light-emitting element 20 may be disposed on the buffer electrode 23, but the present invention is not necessarily limited thereto, and the light-emitting element 20 may also be disposed on the bottom surface of the cavity 11 without the buffer electrode 23.

The buffer electrode 23 may suppress that resistance is increased due to formation of a surface oxide layer, and thus an amount of injected current and an output of light are decreased.

The buffer electrode 23 may contain Au, but the present invention is not necessarily limited thereto.

The light-emitting element may be applied to various types of light source devices. For example, a light source device may have a concept including a sterilization device, a curing device, a lighting device, a display device, a vehicular lamp, and the like. That is, the light-emitting element may be applied to various electronic devices disposed in a case and configured to provide light.

The sterilization device may include the light-emitting element according to the exemplary embodiments to sterilize a desired area. The sterilization device may be applied to household appliances such as a water purifier, an air conditioner, a refrigerator, and the like, but the present invention is not necessarily limited thereto. That is, the sterilization device may be applied to various products requiring sterilization (e.g., medical equipment).

For example, the water purifier may include the sterilization device according to the exemplary embodiments so as to sterilize circulating water. The sterilization device may be disposed at a nozzle or an outlet through which water circulates and may irradiate UV light. In this case, the sterilization device may include a waterproof structure.

The curing device may include the light-emitting element according to the exemplary embodiments to cure various kinds of liquids. The liquids may have the broadest concept that includes various materials which are cured upon exposure to UV light. For example, the curing device may cure various kinds of resins. Alternatively, the curing device may be applied to cure a cosmetic product such as a manicure.

The lighting device may include a light source module having a substrate and the light-emitting element of the exemplary embodiments, a heat dissipation part configured to dissipate heat of the light source module, and a power supplier configured to process or convert an electrical signal provided from the outside to provide the electrical signal to the light source module. In addition, the lighting device may include a lamp, a headlamp, a streetlamp, and the like.

Figure 19:
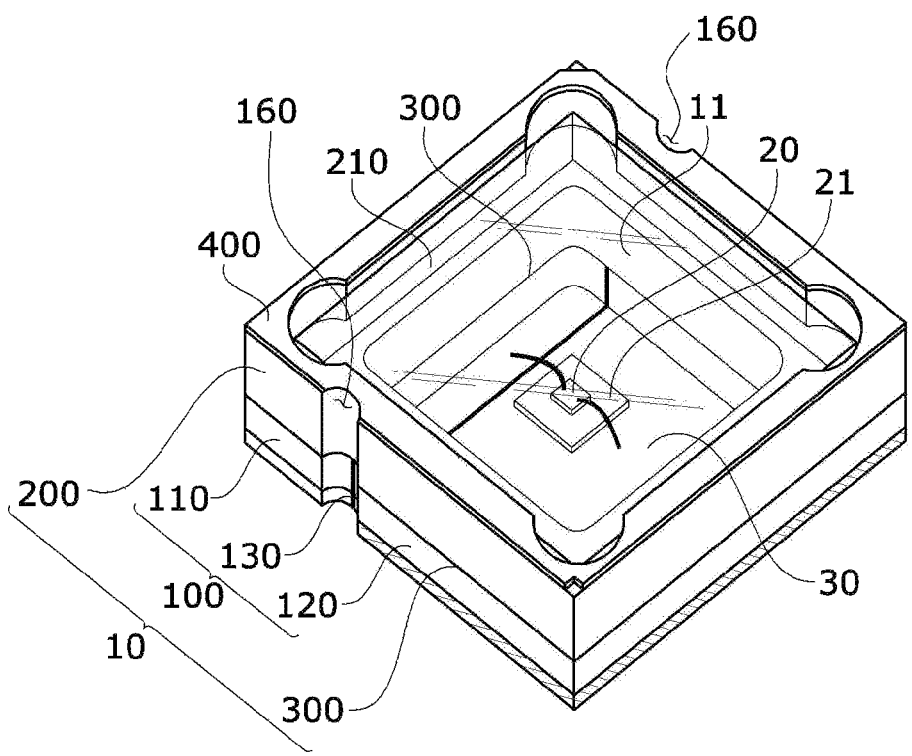
FIG. 19 is a modified example of FIG. 3.
Figure 20:
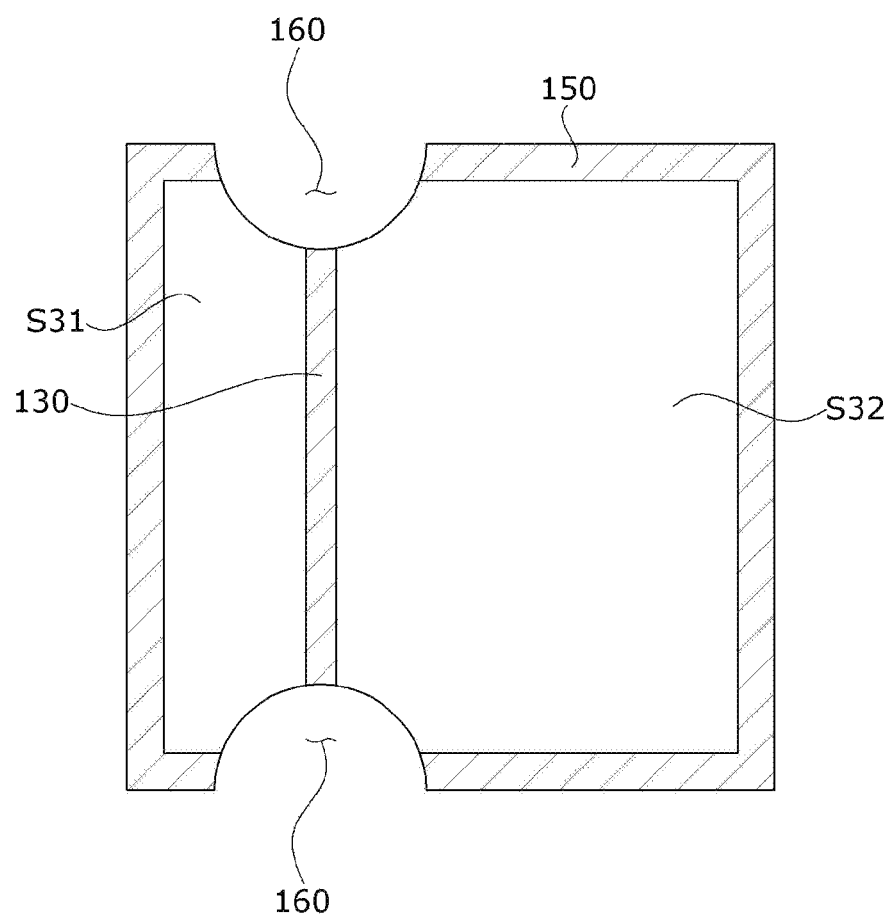
FIG. 20 is a bottom view of FIG. 19.
Figure 21:
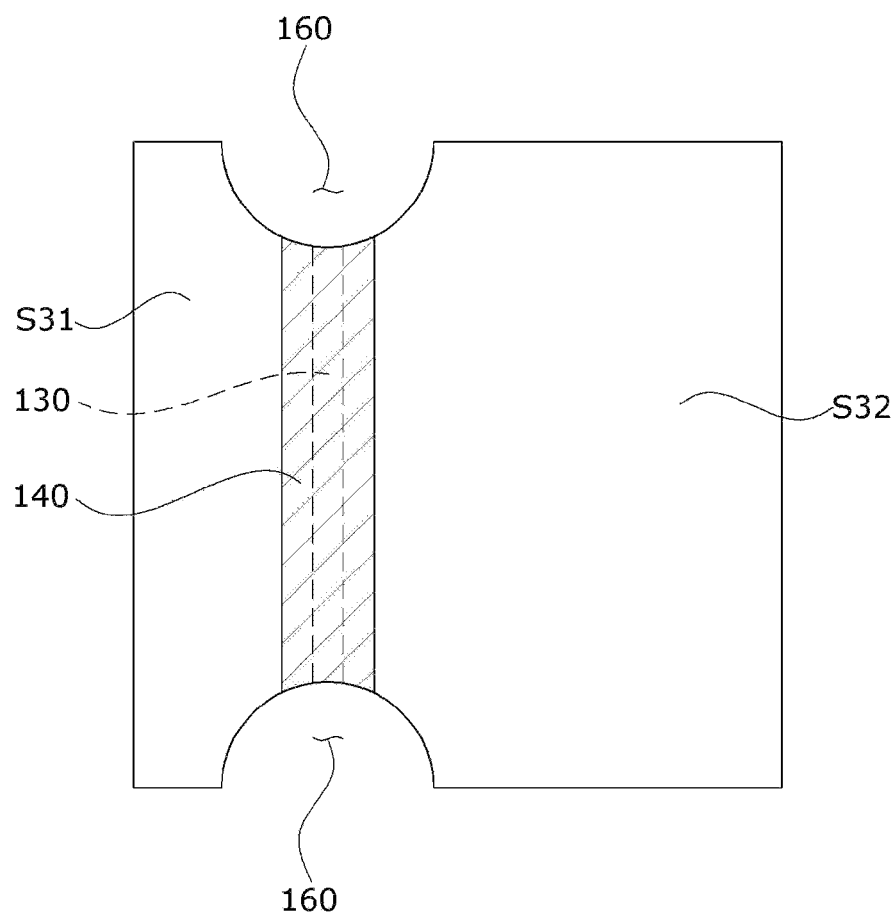
FIG. 21 is a modified example of FIG. 20.

FIG. 19 is a modified example of FIG. 3, FIG. 20 is a bottom view of FIG. 19, and FIG. 21 is a modified example of FIG. 20.

Referring to FIG. 19, a pair of the outer surfaces, which are opposite to each other, of the body 10 may each include a fifth groove 160.

The fifth groove 160 may extend in the first direction (Y direction), and both ends of the fifth groove 160 in the first direction may be open. The first direction (Y direction) may be a direction from the lower surface of the body 10 to the upper surface thereof.

Referring to FIG. 20, both ends of the second insulating portion 150 in contact with the lower surface S31 of the first conductive body may be connected to the fifth groove 160. In addition, both ends of the second insulating portion 150 in contact with the lower surface S32 of the second conductive body may be connected to the fifth groove 160.

The fifth groove 160 may be disposed between an end portion of the second-first insulating portion and an end portion of the second-second insulating portion.

Each of the second-first insulating portion and the second-second insulating portion which are separated by the fifth groove 160 may have a "⊏" shape.

The first insulating portion may be omitted. The first and second grooves in which the first insulating portion is disposed may also be omitted. Thus, the second insulating layer 130 may be exposed to the lower surface of the body 10, and the lower surface S31 of the first conductive body and the lower surface S32 of the second conductive body may be connected to the lower surface of the second insulating layer 130.

Referring to FIG. 21, the first insulating portion 140 may not be omitted, whereas the second insulating portion may be omitted. The third and fourth grooves in which the second insulating portion is disposed may also be omitted. Therefore, the lower surface S31 of the first conductive body and the lower surface S32 of the second conductive body may extend to the outer surface of the body.

While the present invention has been mainly described with reference to the exemplary embodiments, it should be understood that the present invention is not limited to the disclosed exemplary embodiments, and various modifications and applications can be devised by those skilled in the art to which the present invention pertains without departing from the gist of the present invention. For example, each component specifically shown in the exemplary embodiments can be modified and implemented. It should be construed that differences related to these modifications and applications will fall within the scope of the present invention defined by the appended claims.

The invention claimed is:

1. A light-emitting element package comprising:
a body including a cavity; a light-emitting element disposed on a bottom surface of the cavity and including a first conductive type semiconductor layer, a second conductive type semiconductor layer, and an active layer disposed between the first conductive type semiconductor layer and the second conductive type semiconductor layer; and a light-transmitting member disposed in an upper portion of the cavity, wherein the body includes: a lower body including the bottom surface of the cavity; an upper body including a lateral surface of the cavity; and a first insulating layer disposed between the lower body and the upper body, the lower body includes: a first conductive body; and a second conductive body disposed to be insulated from the first conductive body, the first conductive type semiconductor layer is electrically connected to the first conductive body, the second conductive type semiconductor layer is electrically connected to the second conductive body, wherein the lower body includes a first insulating portion disposed in a lower surface groove formed in a lower surface of the lower body such that the first insulating portion is coplanar with a lowermost surface of the lower body, wherein a second insulating layer is disposed between the first conductive body and the second conductive body and connects with the first insulating portion, the first insulating portion and the second insulating layer are made of different materials, wherein: the first conductive body includes a third groove disposed in a corner at which the lower surface of the first conductive body is connected to an outer surface thereof; and the second conductive body includes a fourth groove disposed in a corner at which the lower surface of the second conductive body is connected to an outer surface thereof, wherein the lower body further includes a second insulating portion disposed in the third groove and the fourth groove, and wherein the second insulating portion is coplanar with outermost side surfaces of the first and second conductive bodies, and is coplanar with lowermost surfaces of the first and second conductive bodies.

2. The light-emitting element package of claim 1, wherein a height from a lower surface of the lower body to the bottom surface of the cavity is smaller than a height from the lower surface of the lower body to a lower surface of the first insulating layer, and
wherein a ratio of the height from the lower surface of the lower body to the bottom surface of the cavity to the height from the lower surface of the lower body to the lower surface of the first insulating layer ranges from 1.09:1 to 1.72:1.

3. The light-emitting element package of claim 1, wherein:
each of the first conductive body and the second conductive body includes a side wall protruding toward the upper body; and
the first insulating layer is disposed on the side wall.

4. The light-emitting element package of claim 3, wherein:
an inner surface of the side wall is coplanarly connected to an inner surface of the first insulating layer; and
an inner surface of the first insulating layer is coplanarly connected to an inner surface of the upper body.

5. The light-emitting element package of claim 1, wherein:
each of the first conductive body and the second conductive body contains aluminum (Al); and
the second insulating layer contains polyimide (PI).

6. The light-emitting element package of claim 1, wherein the upper body includes a stepped portion in which the light-transmitting member is disposed.

7. The light-emitting element package of claim 1, wherein the lower surface groove includes:
a first groove formed in the first conductive body and disposed in a corner at which a lower surface of the first conductive body is connected to a surface thereof facing the second conductive body; and
a second groove formed in the second conductive body and disposed in a corner at which a lower surface of the second conductive body is connected to a surface thereof facing the first conductive body.

8. The light-emitting element package of claim 7, wherein the first insulating portion is disposed in the first groove and the second groove.

9. The light-emitting element package of claim 1, further comprising a sub-mount disposed between the bottom surface of the cavity and the light-emitting element.

10. The light-emitting element package of claim 9, wherein:
the sub-mount includes a first pad and a second pad;
a first electrode of the light-emitting element is electrically connected to the first pad; and
a second electrode of the light-emitting element is electrically connected to the second pad.

11. The light-emitting element package of claim 10, wherein:
the first pad is electrically connected to the first conductive body through a wire; and
the second pad is electrically connected to the second conductive body through a wire.

12. The light-emitting element package of claim 11, wherein:
each of a pair of outer surfaces opposite to each other of the body includes a fifth groove; and
the fifth groove is connected to both ends of the second insulating portion in contact with the lower surface of the first conductive body and connected to both ends of the second insulating portion in contact with the lower surface of the second conductive body.

13. The light-emitting element package of claim 12, wherein:
the second insulating portion includes a second-first insulating portion disposed in the third groove and a second-second insulating portion disposed in the fourth groove; and
the fifth groove is disposed between an end portion of the second-first insulating portion and an end portion of the second-second insulating portion.

14. The light-emitting element package of claim 1, wherein the upper body is conductive.

15. The light-emitting element package of claim 1, wherein the light-emitting element emits ultraviolet light.

16. The light-emitting element package of claim 1, wherein a thickness, in a direction perpendicular to the lowermost surfaces of the first and second conductive bodies, of the first insulating portion is smaller than a thickness, in said direction, of the second insulating portion.

17. A light-emitting element package comprising:
a body including a cavity; a light-emitting element disposed on a bottom surface of the cavity and including a first conductive type semiconductor layer, a second conductive type semiconductor layer, and an active layer disposed between the first conductive type semiconductor layer and the second conductive type semiconductor layer; and a light-transmitting member disposed in an upper portion of the cavity, wherein the body includes: a conductive lower body including a bottom surface of the cavity; a conductive upper body including a lateral surface of the cavity; and a first insulating layer disposed between the conductive lower body and the conductive upper body, the conductive lower body includes: a first conductive body, and a second conductive body disposed and insulated from the first conductive body, the first conductive type semiconductor layer is electrically connected to the first conductive body, the second conductive type semiconductor layer is electrically connected to the second conductive body, wherein the conductive lower body includes a first insulating portion disposed in a lower surface groove formed in a lower surface of the conductive lower body such that the first insulating portion is coplanar with a lowermost surface of the conductive lower body, wherein a second insulating layer is disposed between the first conductive body and the second conductive body and connects with the first insulating portion, the first insulating portion and the second insulating layer are made of different materials, wherein: the first conductive body includes a first corner groove disposed in a corner at which the lower surface of the first conductive body is connected to an outer surface thereof; and the second conductive body includes a second corner groove disposed in a corner at which the lower surface of the second conductive body is connected to an outer surface thereof, wherein the lower body further includes a second insulating portion disposed in the first corner groove and the second corner groove, and wherein the second insulating portion is coplanar with outermost side surfaces of the first and second conductive bodies, and is coplanar with lowermost surfaces of the first and second conductive bodies.

18. A light-emitting element package comprising:
a substrate; a light-emitting element package mounted on the substrate; and
a sealing member in contact with an upper surface of the substrate and a lateral surface of the light-emitting element package, wherein the light-emitting element package includes: a body including a cavity; a light-emitting element disposed on a bottom surface of the cavity and including a first conductive type semiconductor layer, a second conductive type semiconductor layer, and an active layer disposed between the first conductive type semiconductor layer and the second conductive type semiconductor layer; and a light-transmitting member disposed in an upper portion of the cavity, the body includes: a lower body including the bottom surface of the cavity; an upper body including a lateral surface of the cavity; and a first insulating layer disposed between the lower body and the upper body, the lower body includes: a first conductive body; and a second conductive body disposed and insulated from the first conductive body, the first conductive type semiconductor layer is electrically connected to the first conductive body, the second conductive type semiconductor layer is electrically connected to the second conductive body, a height from a lower surface of the lower body to the bottom surface of the cavity is smaller than a height from the lower surface of the lower body to a lower surface of the first insulating layer, and a height from the upper surface of the substrate to an upper end of a surface of the sealing member in contact with the body is greater than a height from the upper surface of the substrate to a lower surface of the first insulating layer and is smaller than a height from the upper surface of the substrate to an upper surface of the upper body, wherein the lower body includes a first insulating portion disposed in a lower surface groove formed in a lower surface of the lower body such that the first insulating portion is coplanar with a lowermost surface of the lower body, wherein a second insulating layer is disposed between the first conductive body and the second conductive body and connects with the first insulating portion, the first insulating portion and the second insulating layer are made of different materials, wherein: the first conductive body includes a first corner groove disposed in a corner at which the lower surface of the first conductive body is connected to an outer surface thereof; and the second conductive body includes a second corner groove disposed in a corner at which the lower surface of the second conductive body is connected to an outer surface thereof, wherein the lower body further includes a second insulating portion disposed in the first corner groove and the second corner groove, and wherein the second insulating portion is coplanar with outermost side surfaces of the first and second conductive bodies, and is coplanar with lowermost surfaces of the first and second conductive bodies.

* * * * *